US00PP35547P2

(12) United States Plant Patent
Hartman

(10) Patent No.: US PP35,547 P2
(45) Date of Patent: Dec. 12, 2023

(54) ***CALADIUM* PLANT NAMED 'THAI RD OF14-1145'**

(50) Latin Name: ***Caladium* X *hortulanum***
Varietal Denomination: THAI RD OF14-1145

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/121,512

(22) Filed: Mar. 14, 2023

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. Anne Whealy

(57) ABSTRACT

A new and distinct cultivar of *Caladium* plant named 'THAI RD OF14-1145', characterized by its intermediate in height and upright to mounding plant habit; dense, leafy and bushy appearance; vigorous growth habit and rapid growth rate; lance-type leaves that are dark reddish purple in color with darker-colored venation; first emerging leaves have a metallic sheen; petioles that are close to black in color with pink-colored stripes; and tolerance to full sunlight conditions.

4 Drawing Sheets

Figure 1:
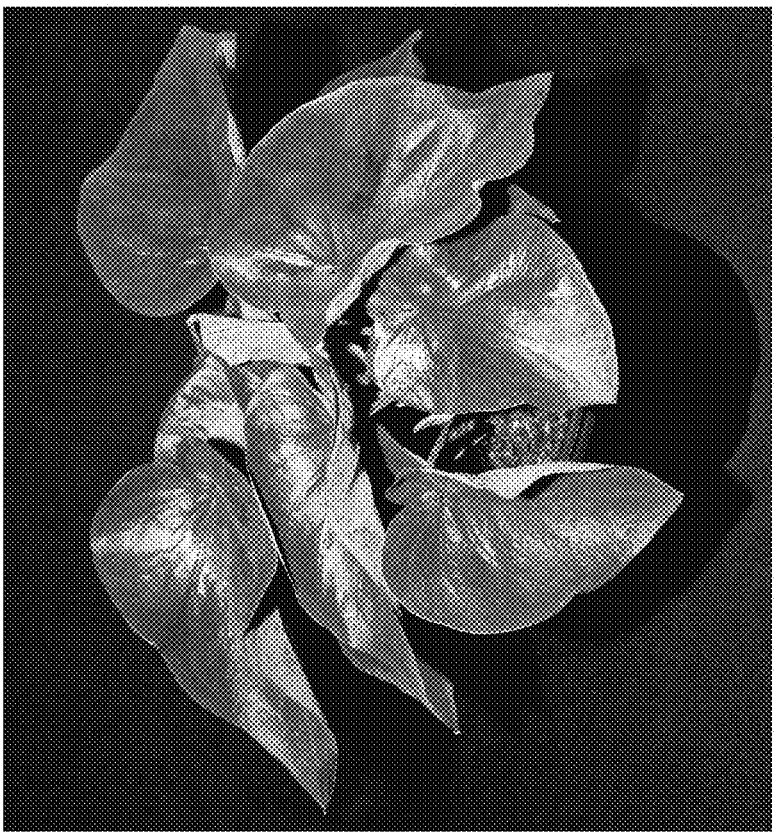

Botanical designation: *Caladium* X *hortulanum*.
Cultivar denomination: 'THAI RD OF14-1145'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'THAI RD OF14-1145'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2013 in Avon Park, Fla. of *Caladium* X *hortulanum* 'Toasted Bronze', not patented, as the female, or seed, parent with *Caladium* X *hortulanum* 'Candy Cane', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2014.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2015 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'THAI RD OF14-1145'. These characteristics in combination distinguish 'THAI RD OF14-1145' as a new and distinct *Caladium* plant:

1. Intermediate in height and upright to mounding plant habit; dense, leafy and bushy appearance.
2. Vigorous growth habit and rapid growth rate.
3. Lance-type leaves that are dark reddish purple in color with darker-colored venation.
4. First emerging leaves have a metallic sheen.
5. Petioles that are close to black in color with pink-colored stripes.
6. Tolerant to full sunlight conditions.

Plants of the new *Caladium* differ primarily from plants of the female parent, 'Toasted Bronze', in the following characteristics:

1. Plants of the new *Caladium* are intetmediate in height whereas plants of 'Toasted Bronze' are short in height.

2. Plants of the new *Caladium* are more vigorous than plants of 'Toasted Bronze'.
3. Leaves of plants of the new *Caladium* are smoother and broader than leaves of plants of 'Toasted Bronze'.
4. Leaves of plants of the new *Caladium* are dark reddish purple in color with darker-colored venation whereas leaves of plants of 'Toasted Bronze' are reddish bronze in color with darker-colored venation.

Plants of the new *Caladium* differ primarily from plants of the male parent, 'Candy Cane', in the following characteristics:

1. Plants of the new *Caladium* are intetmediate in height whereas plants of 'Candy Cane' are short in height.
2. Plants of the new *Caladium* are more vigorous than plants of 'Candy Cane'.
3. Leaves of plants of the new *Caladium* are dark reddish purple in color with darker-colored venation whereas leaves of plants of 'Candy Cane' are greenish white in color variably flushed with light red with dark red to dark greyed purple-colored venation and narrow green-colored margins.
4. Leaf petioles of plants of the new *Caladium* are close to black in color with pink-colored stripes whereas leaf petioles of plants of 'Candy Cane' are green in color tinged with tannish pink.

Plants of the new *Caladium* can be compared to plants of *Caladium* X *hortulanum* 'Burning Heart', disclosed in U.S. Plant Pat. No. 27,071. In side-by-side comparisons, plants of the new *Caladium* differ primarily from plants of 'Burning Heart' in the following characteristics:

1. Leaves of plants of the new *Caladium* are lance types whereas leaves of plants of 'Burning Heart' are fancy types.
2. Leaves of plants of the new *Caladium* are thicker and more cupped than leaves of plants of 'Burning Heart'.
3. Leaves of plants of the new *Caladium* are dark reddish purple in color with darker-colored venation whereas leaves of plants of 'Burning Heart' are bronze red in color with contrasting salmon orange-colored spots and dark red bronze-colored venation.
4. Leaf petioles of plants of the new *Caladium* are close to black in color with pink-colored stripes whereas leaf petioles of plants of 'Burning Heart' are tannish green to tannish pink in color.

Plants of the new *Caladium* can also be compared to plants of *Caladium* X *hortulanum* 'Thai 4', not patented. In side-by-side comparisons, plants of the new *Caladium* differ primarily from plants of 'Thai 4' in the following characteristics:

1. Leaves of plants of the new *Caladium* are lance types whereas leaves of plants of 'Thai 4' are fancy types.
2. Leaves of plants of the new *Caladium* are thicker and more cupped than leaves of plants of 'Thai 4'.
3. Leaves of plants of the new *Caladium* are dark reddish purple in color with darker-colored venation whereas leaves of plants of 'Thai 4' are green with a dark bronze cast in color with reddish bronze-colored centers and numerous coral pink-colored spots.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'THAI RD OF14-1145' grown in a container that has had its tuber de-eyed prior to planting.

Figure 2:
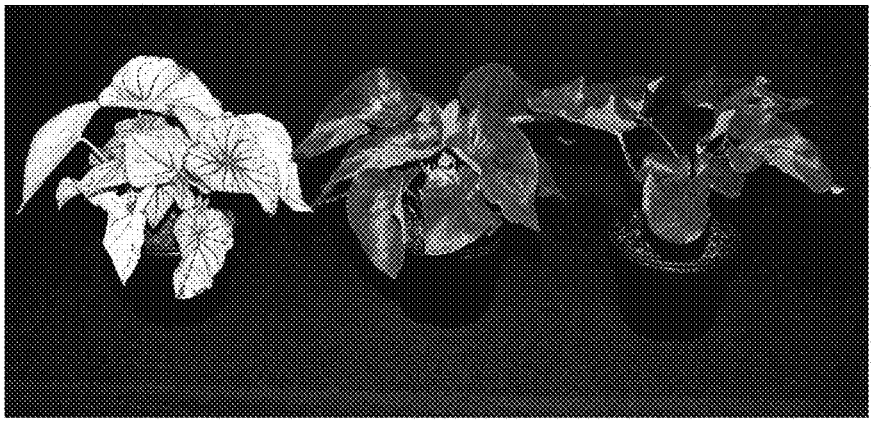

The photograph at the top of the second sheet (FIG. 2) is side perspective view of typical plants of the female parent, 'Toasted Bronze' (right), 'THAI RD OF14-1145' (center) and the male parent, 'Candy Cane' (left).

Figure 3:
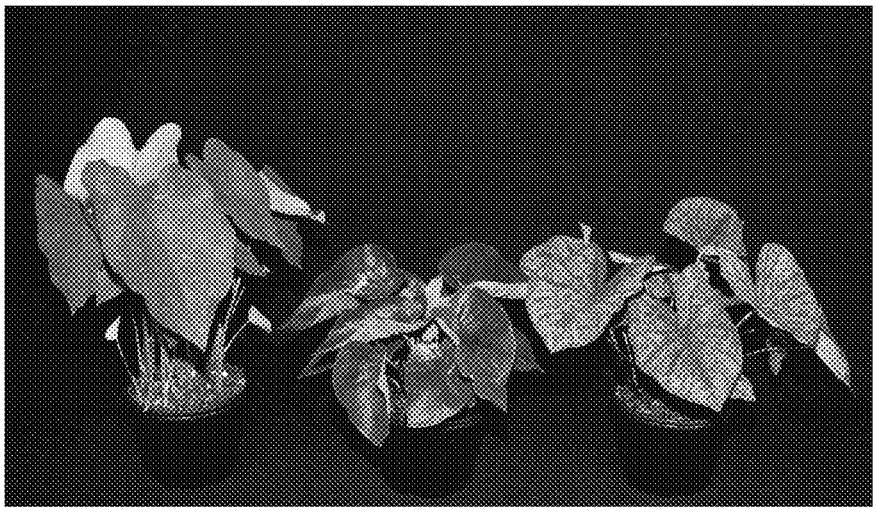

The photograph at the bottom of the second sheet (FIG. 3) is side perspective view of typical plants of 'Burning Heart' (left), 'THAI RD OF14-1145' (center) and 'Thai 4' (right).

Figure 4:
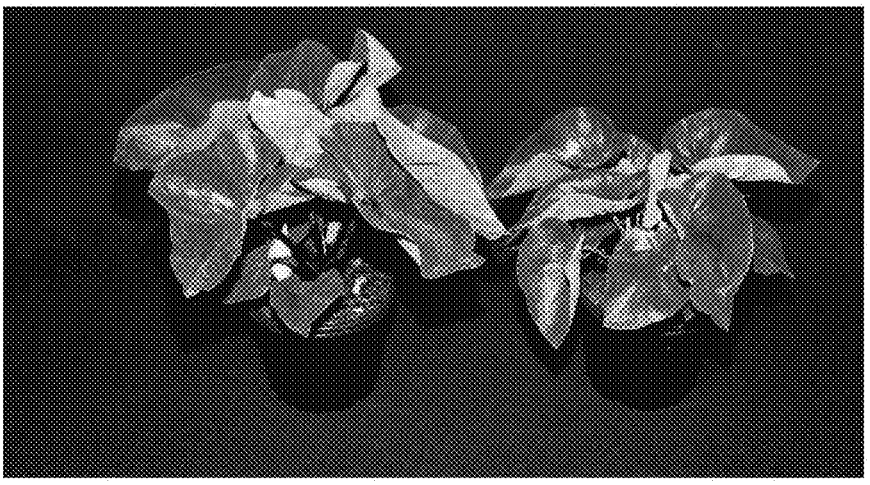

The photograph at the top of the third sheet (FIG. 4) is a comparison view of typical plants of 'THAI RD OF14-1145' grown in containers, the plant on the left has not had its tuber de-eyed and the plant on the right has had its tuber de-eyed prior to planting.

Figure 5:
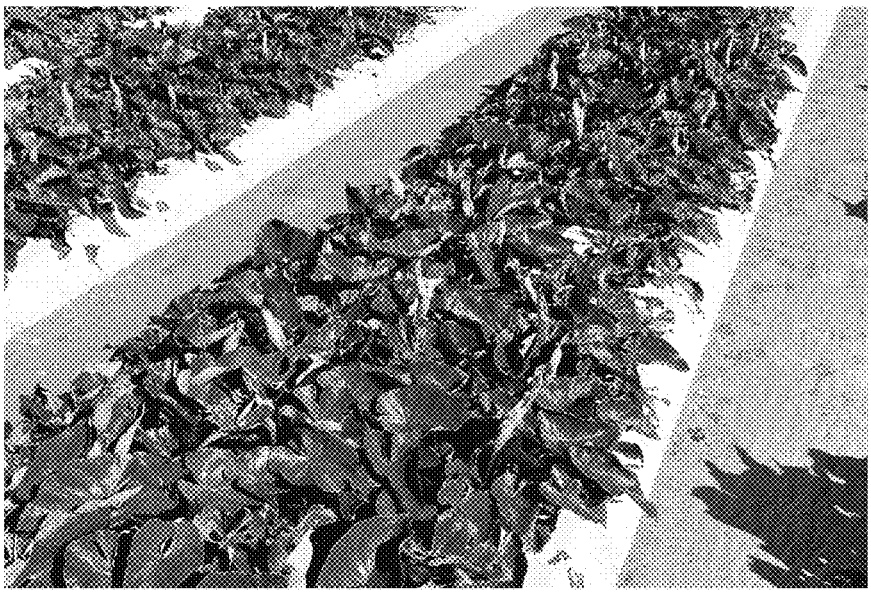

The photograph at the bottom of the third sheet (FIG. 5) is a side perspective view of typical plants of 'THAI RD OF14-1145' grown in an open production field.

Figure 6:
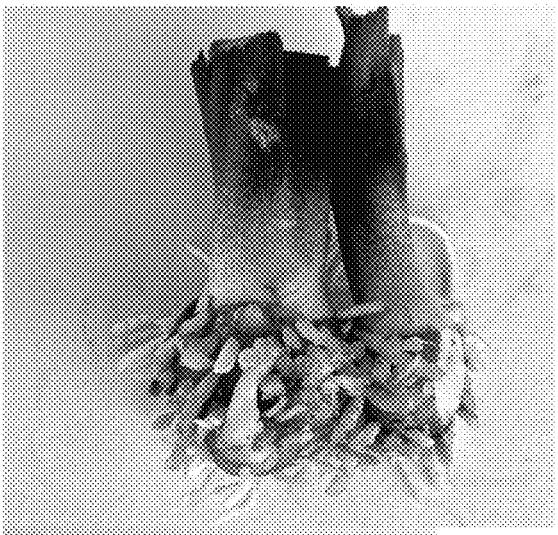

The photograph at the top of the fourth sheet (FIG. 6) is a close-up view of typical freshly-harvested tubers with roots and leaf petioles of 'THAI RD OF14-1145'.

Figure 7:
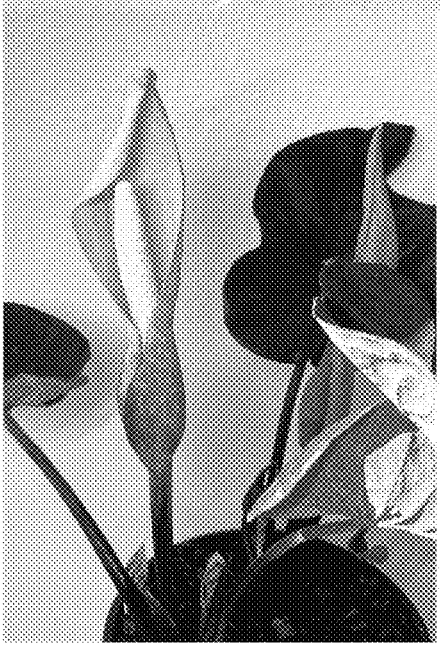

The photograph at the bottom of the fourth sheet (FIG. 7) is a close-up view of a typical flowering plant of 'THAI RD OF14-1145'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28C to 33C, night temperatures ranged from about 22C to 25C and light levels were about 1,300 μmol. During the production of the outdoor nursery-grown plants, day temperatures ranged from about 29C to 35C, night temperatures ranged from about 23C to 26C and full sunlight conditions. Plants grown in the shade house were seven weeks old and plants grown in the outdoor nursery were five months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'THAI RD OF14-1145'.

Parentage:

*Female, or seed, parent.*—*Caladium* X *hortulanum* 'Toasted Bronze', not patented.

*Male, or pollen, parent.*—*Caladium* X *hortulanum* 'Candy Cane', not patented.

Propagation:

*Type.*—By "chipping" the tubers.

*Time to initiate roots, summer.*—About seven to ten days at temperatures about 32C.

*Time to initiate roots, winter.*—About two to three weeks at temperatures about 24C.

*Tuber description* (*outdoor nursery-grown plants*).—Appearance: Multi-segmented, clumping and branched tubers; individual segments are round to ovate in shape. Height: About 2.9 cm to 3.1 cm. Diameter: About 4.1 cm to 5 cm. Segment height: About 2.6 cm. Segment diameter: About 2.2 cm. Axillary bud shape: Roughly triangular. Axillary bud height: About 3.5 mm. Axillary bud width: About 5 mm. Texture: Thick, starchy; somewhat brittle. Color: Periderm, freshly-harvested: Close to N199D. Periderm, dried: Close to 200A. Epidermis: Close to 165C becoming closer to 165D with subsequent development. Cortical tissue: Close to 23C and 23D. Axillary buds: Close to 49C to 49D. Root description: Thick, fleshy contractile roots with few lateral branches; color, close to NN155D; actual color of the roots is dependent on substrate composition, water quality, fertilizer type and fotmulation, substrate temperature and physiological age of roots. Rooting density: Dense.

Plant description:

*Plant type.*—Herbaceous perennial; suitable as a potted plant in containers 15-cm to 25-cm and suitable as a landscape plant in shaded and full sunlight areas.

*Plant and growth habit.*—Intermediate in height and upright to mounding plant habit; plants grown from tubers that have been de-eyed are more mounded than plants grown from tubers that have not been de-eyed; dense, leafy and bushy appearance; vigorous growth habit and rapid growth rate; potted plants finish in saleable form in about six to seven weeks after planting tubers; leaf petioles and leaves arise from one or more growing points on tubers; leaf petioles initially upright and leaning outwardly with development.

*Plant height, from soil level to top of foliar plane, shade house-grown potted plants.*—When de-eyed, about 23.5 cm to 29 cm; when not de-eyed, about 28 cm to 36 cm.

*Plant height, from soil level to top of floral plane, shade house-grown potted plants.*—About 26 cm.

*Plant diameter, shade house-grown potted plants.*—When de-eyed, about 29 cm to 44 cm; when not de-eyed, about 34 cm to 50 cm.

*Number of shoots per plant, shade house-grown potted plants, tubers not de-eyed.*—About one to two develop per #1 tuber.

*Number of shoots per plant, shade house-grown potted plants, tubers de-eyed.*—About seven to nine develop per #1 tuber.

*Cataphylls, shade house-grown potted plants.*—Length: About 4.5 cm to 6 cm. Width: About 1 cm to 1.2 cm. Shape: Linear to lanceolate. Apex: Variable, acute to slightly emarginate. Base: Sheathing the stem. Texture, outer and inner surfaces: Smooth, glabrous. Color, outer surface: Close to 203A or 202A with streaks, close to N170D; color becoming closer to 200A, 200D and/or N200A and may be tinged with close to N186B with subsequent development. Color, inner surface: Close to N155B and N155D; distal end may be flushed with close to 56A; colors and color patterns visible from outer surface.

Leaf description:

*Arrangement and type.*—Alternate; simple; lance-type.

*Length, shade house-grown potted plants.*—When de-eyed, about 13.5 cm to 17 cm; when not de-eyed, about 17.5 cm to 22.3 cm.

*Width, shade house-grown potted plants.*—When de-eyed, about 5 cm to 6.4 cm and flattened, about 10.4 cm to 11.9 cm; when not de-eyed, about 8 cm to 10 cm and flattened, about 11.5 cm to 15.7 cm.

*Shape.*—Broadly ovate; cupped and somewhat conduplicate.

*Apex.*—Acute.

*Base.*—Sagittate-peltate; cordate.

*Margin.*—Entire; mostly flat to somewhat wavy with broad undulations.

*Texture and luster, upper surface.*—Smooth, glabrous; glossy to dull; medium in thickness and somewhat rigid; first emerged leaves are slightly glaucous and metallic in appearance.

*Texture and luster, lower surface.*—Smooth, glabrous; glaucous and dull in sheen.

*Venation pattern.*—Pinnate and palmate.

*Color, shade house-grown potted de-eyed plants.*—Developing leaves, upper surface: Background color: Darker than N186C or close to 187B and 187C; intervenous areas are tinged with close to N199A. Margins: Close to 183A. Basal notch: Close to 183C. Midvein and lateral venation: Close to 202A. Developing leaves, lower surface: Background color: Variably mottled, close to 194A, 194B and 49C flushed with close to 187A. Margins: Similar to background color; edges, close to 49C. Basal notch: Close to 182D and 187A. Midvein and primary veins: Close to 183A streaked and flecked with close to 182C; small veins, close to 187A. Fully expanded leaves, upper surface: Background color: Close to 183A, 183B, 183C and 179A. Margins: Similar to background color with random and variable sectors, close to 147A to 147B. Basal notch: Close to 183C. Midvein and lateral venation: Close to 202A and N186A. Fully expanded leaves, lower surface: Background color: Close to 194B variably tinged, mottled and flushed with close to 187A and 187B. Margins: Similar to background color. Basal notch: Close to 187A. Midvein and primary veins: Close to 183A streaked and flecked with close to 182C; small veins, close to 187A.

*Petioles.*—Aspect: Initially upright and straight, and somewhat outwardly leaning with development; flexible. Length, shade house-grown de-eyed potted plants: About 14.5 cm to 22.2 cm. Length, shade house-grown not de-eyed potted plants: About 16 cm to 27 cm. Diameter, distally, shade house-grown de-eyed potted plants: About 3 mm to 4 mm. Diameter, distally, shade house-grown not de-eyed potted plants: About 6 mm to 6.5 mm. Diameter, proximally, shade house-grown de-eyed potted plants: About 6 mm to 8 mm. Diameter, proximally, shade house-grown not de-eyed potted plants: About 1 cm to 1.2 cm. Texture and luster: Smooth, glabrous and glaucous. Color, shade house-grown potted plants: Close to 203A; may be striped with close to 56D and N170D and stippled with close to 200B; just below the leaf junction, close to 203A; may be streaked with close to 185D. Wing length, shade house-grown potted plants: About 4 cm to 9.5 cm. Wing diameter, shade house-grown potted plants: About 6 mm to 12 mm. Texture and luster, inner and outer surfaces: Smooth, glabrous; dull to slightly glossy. Wing color, shade house-grown potted plants: Outer surface: Close to 203A; streaked and mottled with close to N170D and 56D. Inner surface: Close to N155B and N155D; center, mottled and speckled with close to 187A; margins, flushed with close to N200A and 203A; colors and patterns on the outer surface are visible on the inner surface.

Inflorescence description:

*Inflorescence arrangement.*—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; jasmine-like with mint/camphor note.

*Natural flowering season and flower longevity.*—Plants of the new *Caladium* typically flower during the spring and summer in central Florida; flowers develop about four weeks after growth commences; inflorescences last about three days before fading; inflorescences persistent.

*Spathe.*—Length, overall: About 13.5 cm. Length, distal open portion: About 8.2 cm. Length, proximal closed portion: About 5.3 cm. Width, distal open portion: About 3.7 cm. Depth, distal open portion: About 2.2 cm. Width, at constriction: About 1.5 cm. Width, proximal closed portion: About 2.3 cm. Shape, open portion: Narrowly elliptic to obovate. Apex: Acute. Base: Acute. Margin: Entire. Texture and luster, front surface: Smooth, glabrous; dull sheen. Texture and luster, rear surface: Distally, smooth, glabrous with a dull sheen; proximally, smooth, glabrous, slightly glaucous. Color, front surface: Distal open portion: Close to 157B and 145D; with subsequent development, becoming closer to 199A. Proximal closed portion: Close to 157B; towards the base, flushed with close to N186D; color does not change with subsequent development. Color, rear surface: Distal open portion: Close to 159D and 160D; center, mottled and streaked with close to 147B, 147C and 147D; color does not change with subsequent development. Junction: Close to 200A to 200B tinged with close to N186C. Proximal closed portion: Close to 148C, 177C and 177D variably mottled with close to 200B, 182D and 187A; color does not change with subsequent development.

*Spadix.*—Length, overall: About 8.9 cm. Length, male flower zone: About 5.3 cm. Length, sterile zone: About 1.7 cm. Length, female flower zone: About 1.9 cm. Diameter, male flower zone: About 7 mm. Diameter, sterile flower zone: About 7 mm. Diameter, female flower zone: About 1.1 mm. Shape: Columnar, spindle-shaped. Apex: Blunt, rounded. Base: Obtuse. Aspect: Upright. Color, mature, male zone: Close to 155A. Color, mature, sterile zone: Close to 155D. Color, mature, female zone: Close to 8D and 155D. Male flowers: Quantity per spadix: About 386. Shape: Obovate. Height: About 3 mm. Diameter: About 3.5 mm. Pollen amount: Abundant. Pollen color: Close to 11D. Female flowers: Quantity per spadix: About 220. Shape: Ovate to elliptic. Height: About 2.5 mm. Diameter: About 2 mm. Stigma color: Close to 8D. Ovary color: Close to 155D.

*Scapes.*—Length: About 12.3 cm. Diameter: About 7 mm. Strength: Sturdy; somewhat flexible. Aspect: Mostly erect, straight. Texture and luster: Smooth, glabrous; glossy; distally, glaucous. Color: Close to 202A and N186A; just below spathe, close to N186A.

*Seeds and fruits.*—To date, seed and fruit development have not been observed on plants of the new *Caladium.*

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7C to about 40C and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'THAI RD OF14-1145' as illustrated and described.

* * * * *